US012790584B2

(12) United States Patent
Matsusaki et al.

(10) Patent No.: US 12,790,584 B2
(45) Date of Patent: Nov. 10, 2026

(54) SUPPORTING BATH FOR THREE-DIMENSIONAL (3D) TISSUE CULTURE

(71) Applicant: OSAKA UNIVERSITY, Suita (JP)

(72) Inventors: Michiya Matsusaki, Suita (JP); Donghee Kang, Suita (JP)

(73) Assignee: OSAKA UNIVERSITY, Suita (JP)

(*) Notice: Subject to any disclaimer, the term of this patent is extended or adjusted under 35 U.S.C. 154(b) by 1007 days.

(21) Appl. No.: 17/907,122

(22) PCT Filed: Mar. 25, 2021

(86) PCT No.: PCT/JP2021/014105
§ 371 (c)(1),
(2) Date: Sep. 23, 2022

(87) PCT Pub. No.: WO2021/193981
PCT Pub. Date: Sep. 30, 2021

(65) Prior Publication Data

US 2023/0105586 A1 Apr. 6, 2023

(30) Foreign Application Priority Data

Mar. 26, 2020 (JP) ................................ 2020-056029

(51) Int. Cl.
*C12N 5/00* (2006.01)
*C12N 5/071* (2010.01)
*C12N 5/073* (2010.01)

(52) U.S. Cl.
CPC ......... *C12N 5/0062* (2013.01); *C12N 5/0605* (2013.01); *C12N 5/0625* (2013.01); *C12N 2513/00* (2013.01); *C12N 2533/70* (2013.01)

(58) Field of Classification Search
None
See application file for complete search history.

(56) References Cited

U.S. PATENT DOCUMENTS

| | | | |
|---|---|---|---|
| 2018/0289856 | A1 | 10/2018 | Huang |
| 2019/0093070 | A1 | 3/2019 | Matsusaki |
| 2019/0160203 | A1 | 5/2019 | Gatenholm |
| 2019/0249134 | A1 | 8/2019 | Li et al. |
| 2020/0239824 | A1 | 7/2020 | Huang |

FOREIGN PATENT DOCUMENTS

| | | | |
|---|---|---|---|
| JP | 2001-525826 | A | 12/2001 |
| JP | 2016-39798 | A | 3/2016 |
| JP | 2019-41755 | A | 3/2019 |
| WO | WO 2016/092106 | A1 | 6/2016 |
| WO | WO 2017/049066 | A1 | 3/2017 |
| WO | WO 2017/141691 | A1 | 8/2017 |
| WO | WO 2018/191244 | A1 | 10/2018 |
| WO | WO 2019/199899 | A1 | 10/2019 |

OTHER PUBLICATIONS

International Search Report issued Jun. 8, 2021 in PCT/JP2021/014105, 2 pages.
International Preliminary Report on Patentability and Written Opinion issued Sep. 22, 2022 in PCT/JP2021/014105, (submitting English translation only), 4 pages.
Extended European Search Report dated Jun. 6, 2024 in corresponding European Patent Application No. 21776357.2, 10 pages.
Japanese Office Action Issued Feb. 4, 2025 in Japanese Patent Application No. 2022-510781 (with unedited computer-generated English translation), 13 pages.
Japanese Office Action issued Aug. 26, 2025, in corresponding Japanese Patent Application No. 2022-510781 (with English Translation), 11 pages.
Hinton et al., "Three-dimensional printing of complex biological structures by freeform reversible embedding of suspended hydrogels", Science Advances, 2015, vol. 1, e1500758, pp. 1-10.
Singaporean Office Action issued on Apr. 15, 2026 in the corresponding Singaporean patent application (Application No. 11202253429M) (7 pages).

*Primary Examiner* — Teresa E Knight
(74) *Attorney, Agent, or Firm* — Oblon, McClelland, Maier & Neustadt, L.L.P.

(57) ABSTRACT

[Problem] To provide a supporting bath useful for three-dimensional tissue culture and a method for producing cultured three-dimensional tissue by using the supporting bath. [Solution] Use of a supporting bath for three-dimensional tissue culture, that comprises polymer and water, wherein a thixotropic gel is formed in the bath with the gel being dissolvable in solvent. Also, use of a method for producing the supporting bath.

12 Claims, 4 Drawing Sheets

SUPPORTING BATH FOR THREE-DIMENSIONAL (3D) TISSUE CULTURE

This application claims priority to PCT/JP2021/014105, filed Mar. 25, 2021, claiming priority to Japanese application 2020-056029, filed Mar. 26, 2020, the entire contents of both applications are incorporated herein by reference.

TECHNICAL FIELD

The present invention relates to a supporting bath for three-dimensional (3D) tissue culture and a method for producing a cultured three-dimensional tissue using the same.

BACKGROUND ART

Methods for producing cultured three-dimensional tissues include various methods such as three-dimensional cell layering or three-dimensional (3D) bio-printing now. It has been reported that three-dimensional bio-printing involves use of a gel comprising particles and having thixotropy as a supporting bath (Patent Literature 1). Three-dimensional bio-printing involving use of a supporting bath is useful for maintaining cells or a tissue or preventing the cells or the tissue from drying as compared with conventional three-dimensional bio-printing performed in air, since the cells are disposed within the supporting bath in the three-dimensional bio-printing.

CITATION LIST

Patent Literature

Patent Literature 1: International Publication No. WO 2017/049066

SUMMARY OF INVENTION

Technical Problem

Conventional supporting baths for culturing three-dimensional tissue contains a gel comprising particles and having thixotropy. It is however difficult to prepare the gel comprising the particles, regulate the characteristics of the gel, or remove the gel etc. A bath that contains a gel easy to prepare, regulate the characteristics thereof, or remove etc., and a method for producing a cultured three-dimensional tissue using the same are therefore required.

Means of Solving the Problems

As a result of an earnest investigation to solve the above-mentioned problem, the present inventors have found a supporting bath for culturing three-dimensional tissue, wherein a gel containing a polymer and water and having thixotropy is formed in the bath, the gel being capable of dissolving in a solvent, and have completed the present invention.

Specifically, the present invention provides the following.

[1] A supporting bath for culturing three-dimensional tissue, wherein a gel containing a polymer and water and having thixotropy is formed in the bath, the gel being capable of dissolving in a solvent.

[2] The supporting bath according to [1], wherein a concentration of the polymer is 0.01% by weight or more with respect to a total amount of the water and the polymer.

[3] The supporting bath according to [1] or [2], wherein the polymer is a polysaccharide.

[4] The supporting bath according to [3], wherein the polysaccharide is gellan gum.

[5] The supporting bath according to any one of [1] to [4], wherein the solvent is the water forming the gel or a solution to be added for dissolution.

[6] A method for producing cultured three-dimensional tissue, comprising:

(i) a step of forming a three-dimensional tissue precursor in the supporting bath according to any one of [1] to [5] using three-dimensional bio-printing;

(ii) a step of dissolving the gel of the supporting bath; and (iii) a step of culturing a three-dimensional tissue in an obtained solution.

[7] The method according to [6], wherein the gel is dissolved in the solvent.

[8] The method according to [7], wherein the solvent is the water forming the gel or a solution to be added for dissolution.

[9] The method according to [8], wherein the solution to be added for dissolution is an aqueous tris solution.

Advantageous Effects of Invention

According to the present invention, the gel can be prepared easily and efficiently since the gel can be, for example, prepared from a polymer and water. For example, the gel can be prepared at a high yield or low cost.

According to the present invention, the characteristics of the gel can be regulated since the gel can, for example, be prepared from polymers of various types and various concentrations. For example, the viscosity, permeability, durability, transparency, or color of the gel can be regulated.

According to the present invention, the gel can be dissolved and thus removed since the gel is capable of dissolving in a solvent. For example, the gel can be physically or chemically dissolved in the water forming the gel or a solution to be added for dissolution.

According to the present invention, an excessive or unnecessary amount of the supporting bath incorporated into the cultured three-dimensional tissue can be reduced since the amount of the supporting bath incorporated into the print gel can be reduced.

BRIEF DESCRIPTION OF DRAWINGS

FIG. 1 (*b*) is a schematic diagram of the dissolution of the gel, the removal of the solution and the culture of the formed three-dimensional tissue precursor after the printing. FIG. 1 (*c*) shows that 0.1 wt % gellan gum in DMEM as a solvent is gel-like (left), and 0.1 wt % gelatine in DMEM as a solvent is liquid (right). FIG. 1 (*d*) is the measurement results of the viscosity of the 0.1 wt % gellan gum gel by the shear rate.

FIG. 2 (*b*) shows a photograph after the gellan gum gel was dissolved by a Tris-HCl buffer. FIG. 2 (*c*) shows a photograph after culture for 5 days (left) and a fluorograph after treatment with calcein AM (green fluorescence, viable cells) and ethidium homodimer-1 (red fluorescence, dead cells) for cell survival confirmation (right).

DESCRIPTION OF EMBODIMENTS

Figure 1:
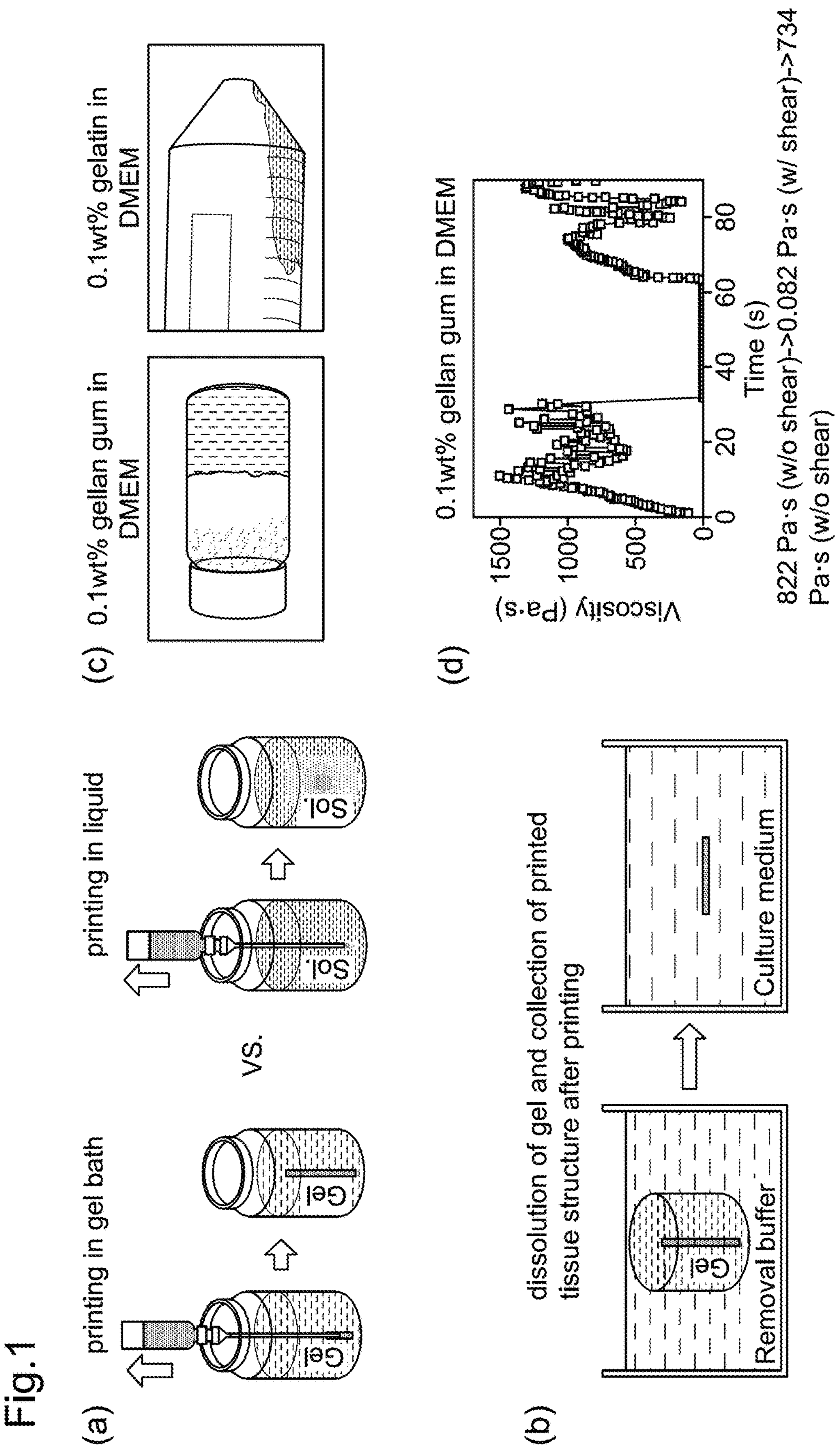
FIG. 1 (*a*) is a schematic diagram of printing in a supporting bath containing a gel or a solution.

In one embodiment, the present invention provides a supporting bath for culturing three-dimensional tissue, wherein a gel containing a polymer and water and having thixotropy is formed in the bath, the gel being capable of dissolving in a solvent.

The thixotropy in the present invention refers to the fluid property characterized in that gel changes into sol by physical stimulus, for example, pressure, and that when the sol is left stand, it returns to gel again (sol-gel transition). Specifically, the thixotropy has the phenomenon of the viscosity decreasing during the shear of liquid, the hysteresis found in the shear stress-shear rate curve of the liquid, and the phenomenon with a yield value. As a device that can determine such characteristics of the thixotropy the best, a stress-controlled rheometer is typically known. A stress-controlled rheometer applies controlled torque (shear stress) to a sample, so that flow begins, and the stress-controlled rheometer measures angular displacement speed (a shear rate), and can obtain the shear stress-shear rate curve easily. This can measure the yield value in the shear stress-shear rate curve extremely accurately unlike other rotational viscometers such as Brookfield viscometers, capillary viscometers, or falling sphere viscometers, which are used generally. For the thixotropy in the present invention, the difference between the viscosities in the presence and the absence of shear stress may be, for example, 0.00001 Pas to 100000 Pas, 0.0001 Pas to 10000 Pas, 0.001 Pas to 1000 Pas, or 0.01 Pas to 100 Pas.

In the present invention, the supporting bath can be rapidly gelated at room temperature or higher temperature. The supporting bath is liquid before gelation, and remains solid during the gelation. For example, the supporting bath becomes liquid by pressure from a nozzle of a dispenser to be used in three-dimensional bio-printing, and returns to gel again after the pressure is removed. Alternatively, for example, three-dimensional bio-printing is performed in a supporting bath in the liquid state before gelation, and the supporting bath may be then subjected to gelation treatment. The supporting bath in the gel state can maintain a three-dimensional tissue precursor. The supporting bath is maintained, for example, under cell survival conditions (for example, temperature and pH). The supporting bath is maintained, for example, under conditions (for example, temperature and pH) that cell growth is not inhibited. The supporting bath is maintained, for example, at 0° C. to 10° C., particularly 4° C., in the liquid state before the gelation. The supporting bath is maintained, for example, at 30° C. to 40° C. particularly 37° C., in the gel state. The supporting bath is maintained, for example, at pH 7.0 to pH 7.8, particularly pH 7.4. The supporting bath may be housed and held in a container, for example, a transparent cylindrical container. The supporting bath may be placed under the sterile condition.

In the present invention, the supporting bath may further contain, for example, culture components for culture a three-dimensional tissue in addition to the polymer and water. The culture components may be covered with a soluble substance, for example, protein such as gelatin. Conditions under which the soluble substance is dissolved may be the same as or different from conditions under which the gel in the supporting bath is dissolved. The soluble substance is dissolved by various stimuli, for example, by time elapse, by physical stimulus, for example, light, temperature or pressure, or, by chemical stimulus, for example, a solution for dissolving the gel, such as a solution containing an enzyme, so that the covered culture components can be released to the bath. For example, the soluble substance can be dissolved under conditions for culturing the three-dimensional tissue, for example, at 37° C., so that the covered culture components can be released to the bath.

In the present invention, the supporting bath may further contain a support for forming a three-dimensional tissue precursor. For example, the support is a scaffold. The three-dimensional tissue precursor is disposed or plotted on the support by the three-dimensional bio-printing. The cultured three-dimensional tissue may be constituted by integrating the three-dimensional tissue precursor and the support. Two or more supports may be disposed, for example, on both ends of the three-dimensional tissue precursor.

In the present invention, the gel is, for example, hydrogel. The hydrogel refers to a substance in which a liquid containing water as a dispersive medium solidifies through sol-gel transition, loses its fluidity, and forms a porous structure.

In the present invention, the gel is a matrix containing a network of hydrophilic polymer chains. The gel is obtained by crosslinking the polymer as a gel material. The gel to be used comprises preferably a hydrophilic polymer crosslinked by cytocompatible crosslinking reaction, for example, a poly(ethylene glycol) (PEG)-based polymer, and the most preferably a multi-arm (that is, branched) PEG-based polymer.

In the present invention, the gel may be an oily gel, and examples include hydrogel. Examples of the polymer as a gel material (a material that forms gel by dispersing the material in water as a dispersive medium) include natural polymers such as agar, gelatin, agarose, xanthan gum, gellan gum, sclerotium gum, gum arabic, tragacanth gum, karaya gum, cellulose gum, tamarind gum, guar gum, locust bean gum, glucomannan, chitosan, carrageenan, quince seeds, galactan, mannan, starch, dextrin, curdlan, casein, pectin, collagen, fibrin, peptides, matrigel, chondroitin sulfate such as sodium chondroitin sulfate, hyaluronic acid (mucopolysaccharide) and hyaluronates such as sodium hyaluronate, alginic acid, alginates such as sodium alginate and calcium alginate, and derivatives thereof; cellulose derivatives such as methyl cellulose, hydroxymethyl cellulose, hydroxyethyl cellulose, hydroxypropyl cellulose, hydroxypropylmethyl cellulose, carboxymethyl cellulose, and salts thereof; poly(meth)acrylic acids such as polyacrylic acid, polymethacrylic acid, acrylic acid-alkyl methacrylate copolymers, and salts thereof; synthetic polymers such as polyvinyl alcohol, a polymer of polyethylene glycol di(meth)acrylate (PPEGDA and PPEGDM), polyhydroxyethyl methacrylate, polyacrylamide, poly(N,N-dimethylacrylamide), poly(2-acrylamide methylpropanesulfonic acid), poly(N-isopropylacrylamide), polyvinylpyrrolidone, polystyrene sulfonate, polyethylene glycol, a carboxyvinyl polymer, an alkyl-modified carboxyvinyl polymer, a maleic anhydride copolymer, polyalkylene oxide-based resin, a crosslinked body of poly(methyl vinyl ether-alt-maleic anhydride) and polyethylene glycol, a crosslinked body of polyethylene glycol, a crosslinked body of N-vinylacetamide, a crosslinked body of acrylamide, and a crosslinked material of a starch-acrylate graft copolymer; silicone; interpenetrating network structural hydrogel and semi-interpenetrating network structural hydrogel (DN hydrogel); and mixtures of two or more thereof.

In the present invention, the polymer as a gel material is, for example, preferably collagen (for example, one or more selected from the group consisting of type I, type II, type III, type IV, type V, and type XI), glucomannan, fibrin, alginic acid, polyvinyl alcohol, PPEGDA, PPEGDM, polyhydroxyethyl methacrylate, polyvinylpyrrolidone, polyacrylamide, poly(N,N-dimethylacrylamide), poly(N-isopropylacrylamide), silicone, DN hydrogel, fibronectin, laminin, elastin, glycosaminoglycan (for example, hyaluronic acid), proteoglycan, gelatin, or a mixture of two or more thereof. In the present invention, the polymer as a gel material may be, for example, nanofiber, for example, cellulose nanofiber. In the present invention, the polymers as a gel material may be used singly or in combination of two or more. In the present invention, the gel may be uniform or homogeneous.

In the present invention, the gel of the polymer may be particle gel (gel particulates) or bulk (straight-chain or linear) gel. Gels are classified into particle gel and bulk gel by the apparent shape of the gel. The gel of the polymer to be used for the supporting bath of the present invention is preferably bulk (straight-chain or linear) gel. Bulk (straight-chain or linear) gel is different from particle gel. The use of the bulk (straight-chain or linear) gel can reduce the amount of the supporting bath incorporated into the print gel, and can therefore reduce an excessive or unnecessary amount of the supporting bath incorporated into the cultured three-dimensional tissue.

In the present invention, the size of the bulk gel is, for example, 0.1 mm or more, 0.5 mm or more, 1.0 mm or more, 5 mm or more, 10 mm or more, 20 mm or more, 30 mm or more, 40 mm or more, 50 mm or more, 100 mm or more, 500 mm or more, or 1000 mm or more, in terms of the longest length (or the shortest length) of the bulk.

In the present invention, the polymer concentration is, for example, 0.001% by weight or more, 0.005% by weight or more, 0.01% by weight or more, 0.05% by weight or more, 0.1% by weight or more, or 1% by weight or more, with respect to the total of water and the polymer. The polymer concentration is, for example, 5.0% by weight or less, 4.5% by weight or less, 4.0% by weight or less, 3.5% by weight or less, 3.0% by weight or less, 2.5% by weight or less, or 2.0% by weight or less, with respect to the total of water and the polymer. The polymer concentration is, for example, 0.001% by weight to 5.0% by weight, 0.001% by weight to 4.5% by weight, 0.001% by weight to 4.0% by weight, 0.001% by weight to 3.5% by weight, 0.001% by weight to 3.0% by weight, 0.001% by weight to 2.5% by weight, 0.001% by weight to 2.0% by weight, 0.005% by weight to 5.0% by weight, 0.005% by weight to 4.5% by weight, 0.005% by weight to 4.0% by weight, 0.005% by weight to 3.5% by weight, 0.005% by weight to 3.0% by weight, 0.005% by weight to 2.5% by weight, 0.005% by weight to 2.0% by weight, 0.01% by weight to 5.0% by weight, 0.01% by weight to 4.5% by weight, 0.01% by weight to 4.0% by weight, 0.01% by weight to 3.5% by weight, 0.01% by weight to 3.0% by weight, 0.01% by weight to 2.5% by weight, 0.01% by weight to 2.0% by weight, 0.05% by weight to 5.0% by weight, 0.05% by weight to 4.5% by weight, 0.05% by weight to 4.0% by weight, 0.05% by weight to 3.5% by weight, 0.05% by weight to 3.0% by weight, 0.05% by weight to 2.5% by weight, 0.05% by weight to 2.0% by weight, 0.1% by weight to 5.0% by weight, 0.1% by weight to 4.5% by weight, 0.1% by weight to 4.0% by weight, 0.1% by weight to 3.5% by weight, 0.1% by weight to 3.0% by weight, 0.1% by weight to 2.5% by weight, or 0.1% by weight to 2.0% by weight, with respect to the total of water and the polymer.

For the present invention, those skilled in the art can suitably regulate the type of the gel and the polymer concentration with respect to the total of water and the polymer, in view of characteristics of the gel, for example, the yield or cost of gel preparation, the viscosity, permeability, durability, transparency, color, or solubility of the gel, or characteristics of cells, for example, the cell type, the biocompatibility, or the cell viability.

In the present invention, when the polymer as a gel material is gellan gum, the polymer concentration is usually 0.01% by weight to 2.0% by weight, for example, 0.05% by weight to 1.0% by weight or 0.08% by weight to 0.5% by weight, preferably 0.1% by weight to 0.2% by weight, for example, 0.11% by weight to 0.19% by weight, 0.12% by weight to 0.18% by weight, or 0.13% by weight to 0.17% by weight, more preferably 0.14% by weight to 0.16% by weight, for example, 0.15% by weight, with respect to the total of water and the polymer.

For example, 70% or more, 75% or more, 80% or more, 85% or more, 90% or more, 95% or more or 100% of the polymer can constitute the gel in the present invention.

For example, the viscosity of the gel can be regulated to a viscosity that enables maintaining the three-dimensional tissue precursor or the three-dimensional tissue in the gel. For example, the viscosity of the gel can be regulated to a viscosity at which the three-dimensional tissue precursor or the three-dimensional tissue does not sink in the gel. For example, the viscosity of the gel is measured using a texture analyzer. The viscosity of the gel can be regulated appropriately, for example, to the strength of the nozzle of the dispenser to be used in three-dimensional bio-printing. The viscosity of the gel is viscosity at which the nozzle of the dispenser is not broken, bent, or deformed.

For example, the permeability of the gel can be regulated to permeability at which water, nutrients and air, and the like can be sent to cells.

For example, the gel can be regulated so as to have high durability to dryness and the like. For example, the gel can be used for 30 minutes or more, 1 hour or more, 1 day or more, 2 days or more, 3 days or more, 4 days or more, 5 days or more, 10 days or more, 15 days or more, or 20 days or more.

For example, the gel has high transparency so as to enable observing the tissue in the gel easily.

For example, the gel is a gel that does not have cytotoxicity or an inhibitory effect on cell behavior, or has low cytotoxicity or a small inhibitory effect on cell behavior.

The gel is dissolved by various stimuli, for example, by time elapse, by physical stimulus, for example, light, temperature or pressure, or by chemical stimulus, for example, a solution for dissolving the gel, such as a solution containing an enzyme. The gel is dissolved in a solvent, for example, water forming the gel or a solution to be added for dissolution. For example, the gel is dissolved in water forming the gel, as a solvent, by an aqueous tris (trishydroxymethylaminomethane) solution. For example, the aqueous tris (trishydroxymethylaminomethane) solution is at around 50 mM.

In the present invention, the polymer of the gel is crosslinked, for example, through crosslinking reaction forming covalent bonds or noncovalent bonds. The crosslinking reaction forming covalent bonds may be enzyme reaction. The crosslinking reaction for forming covalent bonds may be mild chemoselective reaction.

In the present invention, the water may be water containing no impurities or substantially containing no impurities, for example, distilled water, or may be water containing another component, for example, a physiological saline solution or a buffer solution. The buffer solution is, for example, a phosphate-buffered physiological saline solution, a sodium chloride solution, a phosphoric acid solution, water, or a phosphate buffer solution.

In the present invention, the polymer is any polymer that can constitute gel having thixotropy when the polymer is dissolved in water, the gel being capable of then dissolving. The polymer may be a protein, a polysaccharide, or the like. For example, the polymer is a polymer that does not have cytotoxicity or an inhibitory effect on cell behavior, or has low cytotoxicity or a small inhibitory effect on cell behavior. The polysaccharide is, for example, gellan gum.

In the present invention, the solvent is the water forming the gel and/or a solution to be added for dissolution. The gel can be dissolved in the water forming the gel by time elapse or physical stimulus. The gel can be dissolved in a solution to be added for dissolving the gel by chemical stimulus. The solution to be add for dissolving the gel is, for example, a buffer solution that does not have cytotoxicity or an inhibitory effect on cell behavior, or has low cytotoxicity or a small inhibitory effect on cell behavior. The buffer solution is, for example, a phosphate-buffered physiological saline solution, a sodium chloride solution, a phosphoric acid solution, a phosphate buffer, or an aqueous tris(trishydroxymethylaminomethane) solution.

In the present invention, the cells may be cells derived from a human, or may be cells derived from an animal other than a human. The animal is, for example, an insect, a fish, an amphibian, a reptile, a bird or a mammal. The animal is, for example, a frog, a chicken, a human, a monkey, a pig, a horse, a bovine, a sheep, a dog, a cat, a mouse or a rabbit. The animal is, for example, a bovine or a human. The cells are, for example, cells derived from mesenchymal stem cells, embryonic stem cells, induced pluripotent stem cells, or the like. The cells are, for example, cells derived from healthy cells or unhealthy cells. The cells may be cultured cells. Examples of the cultured cells include primary culture cells, subcultured cells, and cell line cells. The cells may be cells derived from any tissue. The cells are, for example, skin fibroblasts, umbilical vein endothelial cells, muscle cells or myoblasts.

In the present invention, the three-dimensional tissue is, for example, a cellular aggregate containing cultured cells and an extracellular matrix. The three-dimensional tissue is, for example, a matured tissue or an organ. The three-dimensional tissue may further have a vasculature. The three-dimensional tissue may be any tissue, and is, for example, an epithelial tissue, a connective tissue, a muscular tissue, or a nervous tissue. The three-dimensional tissue is, for example, an epithelial tissue or a muscular tissue. The three-dimensional tissue may be any organ, and, is, for example, an intestine, a stomach, a liver, a pancreas, a lung, a heart, or a brain. The three-dimensional tissue comprises two or more, for example, 2, 5, 10, 20, 30, 40, 50, 100, or 500 or more cells. The three-dimensional tissue comprises, for example, 1000, 5000, or 10000 or less cells. The three-dimensional tissue may form a three-dimensional structure in which cells are disposed with an extracellular matrix.

In the present invention, the tissue precursor is, for example, in a state before a matured tissue is formed. For example, the tissue precursor is a premature cell population formed in the supporting bath using three-dimensional bio-printing.

In the present invention, the extracellular matrix may contain a substance that can play a role in in vitro cell culture or a substance synthesized artificially. The extracellular matrix includes, but is not limited to, fibronectin, gelatin, collagen, laminin, poly-lysine, and the like. The extracellular matrix may be one or more. The extracellular matrix may form intercellular adhesion between adjoining cells.

The present invention provides a method for producing a cultured three-dimensional tissue using the above-mentioned supporting bath in one embodiment. This method comprises:

(i) a step of forming a three-dimensional tissue precursor in the above-mentioned supporting bath using three-dimensional bio-printing,
(ii) a step of dissolving a gel of the supporting bath, and
(iii) a step of culturing a three-dimensional tissue in the obtained solution.

In the present invention, the method for producing a cultured three-dimensional tissue enables culturing the formed three-dimensional tissue precursor to produce a three-dimensional tissue.

In the step (i), the three-dimensional bio-printing is a process in which cells for forming the three-dimensional tissue precursor are disposed or plotted in the supporting bath. The three-dimensional bio-printing may be an automatic or semiautomatic process supported by a computer, or may be a manual process. For example, the three-dimensional bio-printing is a method for disposing or plotting cells in the supporting bath using a dispenser having a nozzle, for example, a multi-nozzle dispenser. The multi-nozzle dispenser can dispose or plot, for example, 2, 4, 8, 16, or 32 cells at once. Cells can be ejected to predetermined positions in the supporting bath by the nozzle. The nozzle caliber has a size that disposed or plotted cells can pass or a larger size, for example, 5 μm or more, 10 μm or more, 50 μm or more, 100 μm or more, 500 μm or more, or 1000 μm or more. The traveling speed of the nozzle is, for example, 0.1 mm/s or more, 0.5 mm/s or more, 1 mm/s or more, 2 mm/s or more, or 5 mm/s or more. The traveling speed of the nozzle is, for example, 20 mm/s or less, 10 mm/s or less, 5 mm/s or less, 2 mm/s or less, or 1 mm/s or less.

The above-mentioned step (i) is performed, for example, at 0° C. to 40° C. In the step (i), the supporting bath is maintained at temperature at which cells are preserved, for example, at 30° C. to 40° C., particularly at 37° C., after the three-dimensional bio-printing. In the above-mentioned step (i), the three-dimensional tissue precursor may be matured and stabilized to form and preserve the three-dimensional tissue precursor while the three-dimensional tissue precursor is being formed.

In the above-mentioned step (ii), the supporting bath can be removed from the three-dimensional tissue by dissolving the gel of the supporting bath in the solvent. For example, this measure enables removing the supporting bath from the three-dimensional tissue more delicately, easily, and rapidly as compared with when the supporting bath is physically removed (for example, shaven or washed) from the three-dimensional tissue. For example, this measure is unlikely to damage the three-dimensional tissue as compared with when the supporting bath is physically removed (for example, shaven or washed) from the three-dimensional tissue. The gel may be dissolved in the solvent over 3 days or less, 24 hours or less, 12 hours or less, 6 hours or less, 3 hours or less, or 1 hour or less.

The above-mentioned step (ii) may comprise removing the dissolved gel after the gel is dissolved.

In the above-mentioned step (iii), culture components for culturing a three-dimensional tissue may be added.

The above-mentioned step (iii) may further comprise inducing differentiation of a three-dimensional tissue, electrically stimulating the three-dimensional tissue, and/or confirming the survival of the cells.

The above-mentioned step (iii) refers to a step of preserving the cells under conditions suitable for maintenance, growth, and/or differentiation. The conditions, for example, refer to the temperature for preserving the cells, culture components, the CO2 content, and the confluency. The conditions are, for example, 37° C. and 5% CO2.

Although the present invention will be described in detail further specifically by illustrating Examples below, it should not be understood that the scope of the present invention is limited to these Examples.

EXAMPLES

Example 1

1. Preparation of Gellan Gum Gel

First, 10 mg of gellan gum (gellan gum (KELCOGEL AFT)/Sansho Co., μLtd./-/Lot. #4H9829A) was dissolved in 8.9 mL of $Ca^{2+}$-free DMEM (DMEM/Thermo Fisher Scientific K.K./10569010) (10% FBS (FBS/Corning Incorporated/35 CV) and 1% antibiotics (antibiotics/NACALAI TESQUE, INC./02892-54)) at 100 degrees Celsius to prepare a 0.1 wt % gellan gum solution. Then, 1 mL of FBS and 100 μL of antibiotics were added. Then, 2.65 mg of $CaCl_2$ was added. The prepared gellan gum gel was gel-like (see FIG. 1 (*c*)).

2. Preparation of Gelatin Solution

First, 10 mg of gelatin was mixed in 10 mL of DMEM (10% FBS, 1% antibiotics), and the gelatin was then dissolved at 37 degrees Celsius for one hour to prepare a gelatin solution. The prepared gelatin solution was liquid (see FIG. 1 (*c*)).

3. Determination of Rheological Characteristic of Gellan Gum Gel

The viscosity by the shear rate was measured to determine the thixotropy. Around 800 μL of the gellan gum gel was loaded on a rheometer plate (Thermo Scientific HAAKE RheoStress 6000, Thermo Fisher Scientific K.K.), and the viscosity was then measured at a shear rate of 0.01/s for initial 30 seconds and a shear rate of 100/s for subsequent 30 seconds, and a shear rate of 0.01/s was then applied again. The 0.1 wt % gellan gum gel had high viscosity initially (around 822 Pa·s). When shearing force was applied, the viscosity decreased sharply (around 0.082 Pa·s), and the gellan gum gel became liquid. When the shear force was removed, the viscosity increased again (around 734 Pa·s), (see FIG. 1 (*d*)).

Example 2

1. Production of Supporting Bath of Gellan Gum

First, 0.15 wt % of gellan gum was dissolved in PBS 1× at 100 degrees Celsius, and a gel was formed in a printing container.

2. Cell Culture

Skin fibroblasts were cultured in culture medium (DMEM, 10% FBS, 1% antibiotics) in a culture flask for adherent cells. When the cells in the culture flask grew to a confluency of 80% or more, the cells were subcultured and proliferated.

Human umbilical vein endothelial cells were cultured in the culture flask for adherent cells in the same way as the skin fibroblasts except that culture medium (EGM-2) was used.

3. Preparation of Bioink

The skin fibroblasts and the human umbilical vein endothelial cells were collected from the culture flasks to prepare a bioink having the following composition. Skin fibroblasts: $6.6\times10^5$ cells/mL, human umbilical vein endothelial cells: $3.4\times10^5$ cells/mL, collagen microfiber: 1.2 wt %, and fibrinogen: 5 mg/mL.

4. Cell Printing

Figure 2:
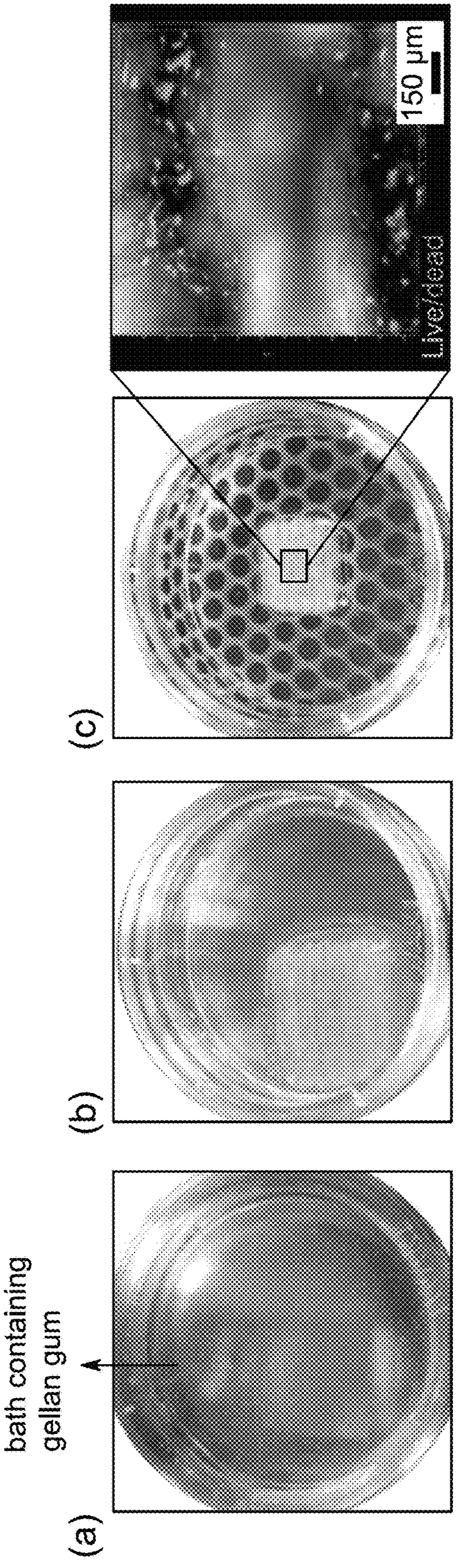
FIG. 2 (*a*) shows a photograph after the three-dimensional cell printing in 0.15 wt % gellan gum gel dissolved in PBS1× in a supporting bath.

A syringe was charged with the prepared bioink, and cell printing was performed in the form of a continuous line in the supporting bath. In the printing, a 22 G nozzle (0.39 mm in inner diameter, 0.72 mm in outer diameter) was used, and the traveling speed was 2 mm/s. Around 450 μL of the bioink was used (see FIG. 2 (*a*)). After the printing, the cells were incubated at 37 degrees Celsius for 20 minutes. The gellan gum gel in the supporting bath was then treated with a Tris-HCl buffer (pH 7.4, 50 mM) at 37 degrees Celsius for 1 hour to dissolve (see FIG. 2 (*b*)), and the solution in the supporting bath was removed. Culture medium obtained by mixing the culture medium for skin fibroblasts and the culture medium for human umbilical vein endothelial cells at 1:1 was added, and the cells were cultured.

5. Cell Viability Measurement

After the cell culture for 7 days, the culture medium was removed, and the cells were washed with PBS1×. After the washing, the cells were treated with a stain solution (2 μM Calcein AM and 4 μM Ethidium homodimer-1 in PBS1×) at 37 degrees Celsius for 15 minutes. After the washing with PBS1×, the three-dimensional tissue was photographed using a confocal laser microscope (see FIG. 2 (*c*)).

Example 3

1. Preparation of Supporting Bath of Particle Gel or Bulk Gel (Straight-Chain Gel)

A support bath was produced by using gellan gum (GG) dissolved in PBS at a predetermined concentration. 1 wt % of GG was dissolved, and the resultant was cooled to room temperature and treated with a homogenizer for 6 minutes to obtain a particle gel having a particle size of 20 μm. The resulting particle gel was subjected to further sonication treatment to obtain a particle gel having a particle size of 6 μm. Furthermore, olive oil and span 80 were dispersed in the aqueous GG solution to thereby produce a W/O emulsion, and the emulsion was gelated to obtain a particle gel having a particle size of 50 nm. A 0.15 wt % GG solution was heated and then cooled to room temperature to produce a bulk gel bath. Fluorescein-modified GG (F-GG) was added to each supporting bath so that the supporting bath contained 0.015 wt % of F-GG, thereby preparing fluorescence-labeled supporting baths.

2. Confirmation of Amount of Supporting Bath Incorporated into Print Gel

Figure 3:
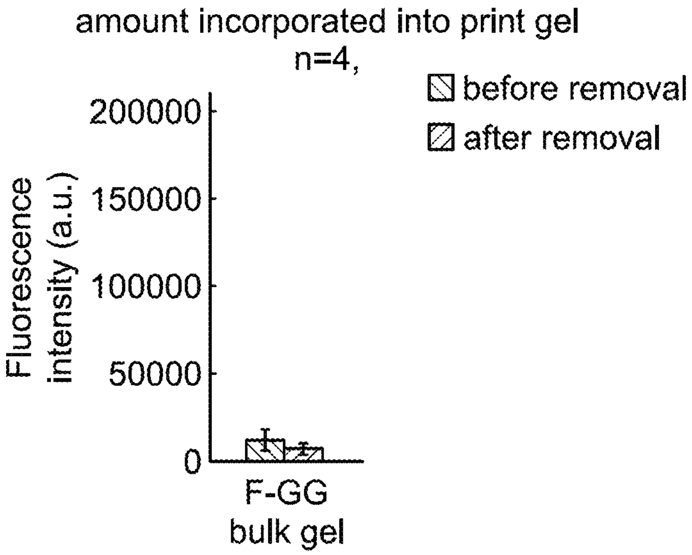
FIG. 3 shows the results of fluorescence intensities (a. u.) obtained before and after the removal by Tris-HCl when F-GG bulk gel (straight-chain gel) was used, that is, the results of the amounts of the supporting bath incorporated into the print gel.

A PBS solution containing 2% by weight of fibrinogen and thrombin at 0.6 U/ml were printed in each fluorescence-labeled supporting bath, and the resulting supporting bath was gelated for one hour to obtain cylindrical gel. The obtained print gel was collected, gently washed with PBS, and then three-dimensionally observed with a confocal laser scanning microscope to observe fluorescence GG incorporated into the print gel. The print gel was immersed in 40 mL of 50 mM Tris-HCl for 1 day. The print gel was further immersed in 40 mL of 50 mM fresh Tris-HCl for 1 day. The obtained print gel was dissolved using trypsin, and the fluorescence intensity (a. u.) of the resulting solution was quantified by the fluorescence spectrum. FIG. 3 shows the results of the obtained fluorescence intensities before and after the removal by Tris-HCl (a. u.). The amount of the supporting bath incorporated into the print gel decreased with increase in particle size. The amount of the supporting bath of the F-GG bulk gel incorporated into the print gel was smaller than the amounts of the supporting baths of the F-GG particle gels incorporated into the print gel.

3. Measurement of Recovered Viscosity

Figure 4:
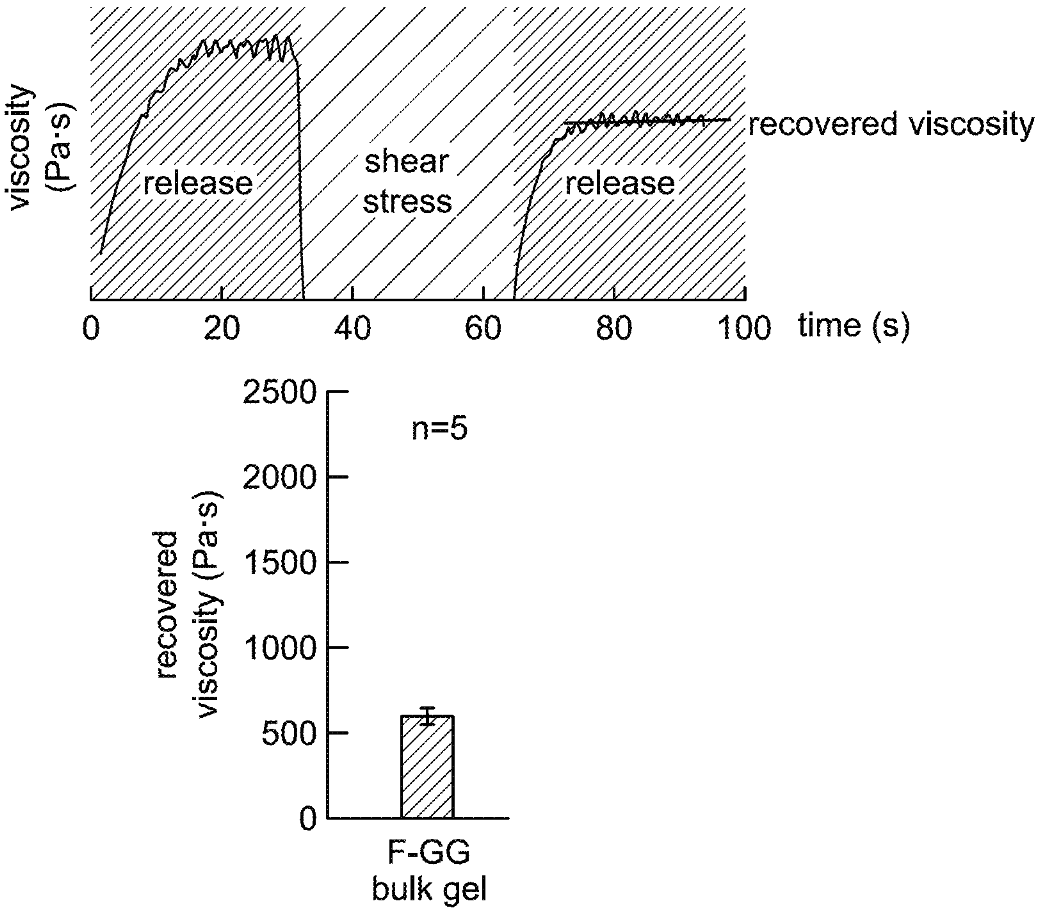
FIG. 4 shows the recovered viscosity when F-GG bulk gel (straight-chain gel) was used.

The viscosity by the shear rate was measured to determined the thixotropy. Around 800 μL of the gellan gum gel was loaded on a rheometer plate (Thermo Scientific HAAKE RheoStress 6000, Thermo Fisher Scientific K.K.), and the viscosity was then measured at a shear rate of 0.01/s for initial 30 seconds and a shear rate of 100/s for subsequent 30 seconds, and a shear rate of 0.01/s was then applied again. The recovered viscosity increased with increase in particle size. The recovered viscosity is viscosity measured after a shear rate of 0.01/s was applied again. The F-GG bulk gel has lower recovered viscosity than the F-GG particle gels. Regarding to F-GG particle gel, it was found that as the recovered viscosity was higher, the amount of the F-GG particle gel incorporated was reduced. Although the F-GG bulk gel had a low recovered viscosity, the amount of the supporting bath of the F-GG bulk gel incorporated into the print gel was smaller than the amounts of the supporting baths of the F-GG particle gels incorporated into the print gel (see FIG. 4).

Example 4

1. Confirmation of Sol-Gel Transition of Supporting Bath

For a supporting bath of bulk gel (straight-chain gel) of 0.15 wt % by gellan gum (GG), the storage elastic modulus (G') and the loss elastic modulus (G") were measured dependently on frequency using a rheometer plate (Thermo Scientific HAAKE RheoStress 6000, Thermo Fisher Scientific K.K.). The conditions used were as follows. Conditions: p20 TiL (20 mm in diameter, flat plate); 300 μL; gap=0.5 mm; mode=CS; $\tau$=10.0 Pa; frequency=0.1 to 10 Hz; T=20° C.

Figure 5:
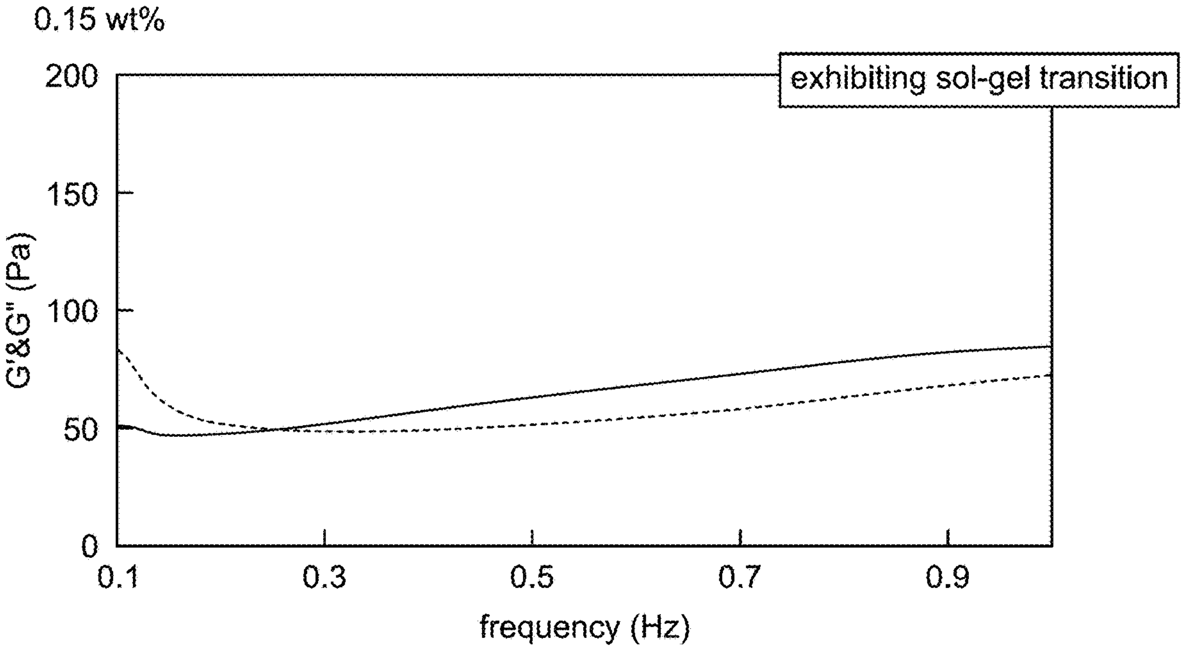
FIG. 5 shows the results of sol-gel transition in the supporting bath containing a bulk gel (straight-chain gel) of 0.15 wt % gellan gum (GG).

FIG. 5 shows that the supporting bath of the 0.15 wt % straight-chain gellan gum (GG) exhibits sol-gel transition. In FIG. 5, the greenish blue line shows the storage elastic modulus (G'), and the dark blue line shows the loss elastic modulus (G").

The invention claimed is:

1. A method for producing cultured three-dimensional tissue, the method comprising:

(i) forming a three-dimensional tissue precursor in a supporting bath by ejecting a bioink comprising cells from a nozzle dispenser into a gel formed in the supporting bath while moving the nozzle at a traveling speed of at least 0.1 mm/s;

wherein the gel is a bulk gel comprising a polymer and water and having thixotropy, wherein the gel is capable of dissolving in a solvent, wherein the gel comprises a polysaccharide as the polymer, and wherein a concentration of the polysaccharide is from 0.001% by weight to 5% by weight with respect to a total amount of the water and the polysaccharide;

(ii) dissolving the gel in the supporting bath; and (iii) in a solution obtained by dissolving the gel, culturing the formed three-dimensional tissue precursor to produce a three-dimensional tissue, and culturing the three-dimensional tissue.

2. The method for producing cultured three-dimensional tissue according to claim 1, wherein the gel is dissolved in the solvent.

3. The method for producing cultured three-dimensional tissue according to claim 2, wherein the solvent is the water forming the gel or a solution to be added for dissolution.

4. The method for producing cultured three-dimensional tissue according to claim 3, wherein the solution to be added for dissolution is an aqueous tris solution.

5. The method for producing cultured three-dimensional tissue according to claim 1, wherein the concentration of the polymer is from 0.05% by weight to 2.0% by weight with respect to a total amount of the water and the polymer.

6. The method for producing cultured three-dimensional tissue according to claim 1, wherein the polysaccharide is gellan gum.

7. The method for producing cultured three-dimensional tissue according to claim 1, wherein the gel is dissolved using an aqueous tris(hydroxymethyl)aminomethane solution.

8. A method for producing cultured three-dimensional tissue, the method comprising:

(i) forming a three-dimensional tissue precursor in a supporting bath by ejecting a bioink containing cells from a nozzle dispenser into a gel formed in the supporting bath while moving the nozzle at a traveling speed of at least 0.1 mm/s;

wherein the gel is a bulk gel containing a polymer and water and having thixotropy, wherein the gel is capable of dissolving in a solvent, wherein the gel comprises a polysaccharide as the polymer, and wherein a concentration of the polysaccharide is from 0.001% by weight to 5% by weight with respect to a total amount of the water and the polysaccharide;

(ii) dissolving the gel in the supporting bath;

(iii) removing the dissolved gel after the dissolution;

(iv) adding a culture medium comprising a culture component for culturing the three-dimensional tissue; and (v) culturing the formed three-dimensional tissue precursor to produce a three-dimensional tissue and culturing the three-dimensional tissue in the culture medium.

9. The method for producing cultured three-dimensional tissue according to claim 8, wherein the gel is dissolved in the solvent.

10. The method for producing cultured three-dimensional tissue according to claim 8, wherein the concentration of the polymer is 0.05% by weight to 2.0% by weight with respect to a total amount of the water and the polymer.

11. The method for producing cultured three-dimensional tissue according to claim 8, wherein the polysaccharide is gellan gum.

12. The method for producing cultured three-dimensional tissue according to claim 8, wherein the gel is dissolved using an aqueous tris(hydroxymethyl)aminomethane solution.

* * * * *